(12) United States Patent
Lorenzo et al.

(10) Patent No.: US 7,344,558 B2
(45) Date of Patent: Mar. 18, 2008

(54) EMBOLIC DEVICE DELIVERY SYSTEM

(75) Inventors: Juan A. Lorenzo, Davie, FL (US); Vladimir Mitelberg, Aventura, FL (US); Donald K. Jones, Lauderhill, FL (US)

(73) Assignee: Cordis Development Corporation, Miami Lakes, FL (US)

( * ) Notice: Subject to any disclaimer, the term of this patent is extended or adjusted under 35 U.S.C. 154(b) by 66 days.

(21) Appl. No.: 11/364,462

(22) Filed: Feb. 28, 2006

(65) Prior Publication Data

US 2007/0203519 A1   Aug. 30, 2007

(51) Int. Cl.
*A61F 2/06*   (2006.01)
*A61F 2/02*   (2006.01)

(52) U.S. Cl. .................................... 623/1.11
(58) Field of Classification Search .............. 606/200, 606/191, 151, 108, 157; 623/23.72
See application file for complete search history.

(56) References Cited

U.S. PATENT DOCUMENTS

| | | | |
|---|---|---|---|
| 2,638,365 A | 5/1953 | Jones | |
| 3,429,408 A | 2/1969 | Maker | |
| 5,108,407 A | 4/1992 | Geremia et al. | |
| 5,217,438 A | 6/1993 | Davis et al. | |
| 5,234,437 A | 8/1993 | Sepetka | |
| 5,350,397 A * | 9/1994 | Palermo et al. | 606/200 |
| 5,476,493 A * | 12/1995 | Muff | 607/119 |
| 5,571,089 A | 11/1996 | Crocker | |
| 5,725,546 A | 3/1998 | Samson | |
| 5,765,449 A | 6/1998 | LeMire | |
| 5,989,242 A | 11/1999 | Saadat et al. | |
| 6,203,547 B1 | 3/2001 | Nguyen et al. | |
| 6,478,773 B1 | 11/2002 | Gahndi et al. | |
| 6,562,064 B1 | 5/2003 | deBeer | |
| 2002/0099408 A1 | 7/2002 | Marks et al. | |
| 2004/0172053 A1* | 9/2004 | Barry et al. | 606/195 |
| 2004/0199175 A1* | 10/2004 | Jaeger et al. | 606/108 |
| 2005/0149108 A1* | 7/2005 | Cox | 606/200 |
| 2005/0216049 A1* | 9/2005 | Jones et al. | 606/200 |
| 2006/0025801 A1* | 2/2006 | Lulo et al. | 606/200 |
| 2006/0025803 A1* | 2/2006 | Mitelberg et al. | 606/200 |

* cited by examiner

*Primary Examiner*—Michael J. Hayes
*Assistant Examiner*—Christina Gettman
(74) *Attorney, Agent, or Firm*—Michael W. Montgomery

(57) ABSTRACT

A vascular occlusion device deployment system for deploying an occlusion device at a preselected site within the vasculature of a patient. The deployment system includes a pusher which has a constrictor located at the distal end portion of the pusher. The constrictor has a channel which receives a portion of the occlusion device. The constrictor has a proximal end portion and a distal end portion wherein the proximal end portion can be moved relative to the distal end portion to reduce the size of the channel. When the channel size is reduced, the constrictor grasps the portion of the occlusion device located within the channel. When it is desired to deploy the coil, the constrictor is moved in the opposite direction to increase the size of the channel and release the coil's grasp of the occlusion device.

22 Claims, 3 Drawing Sheets

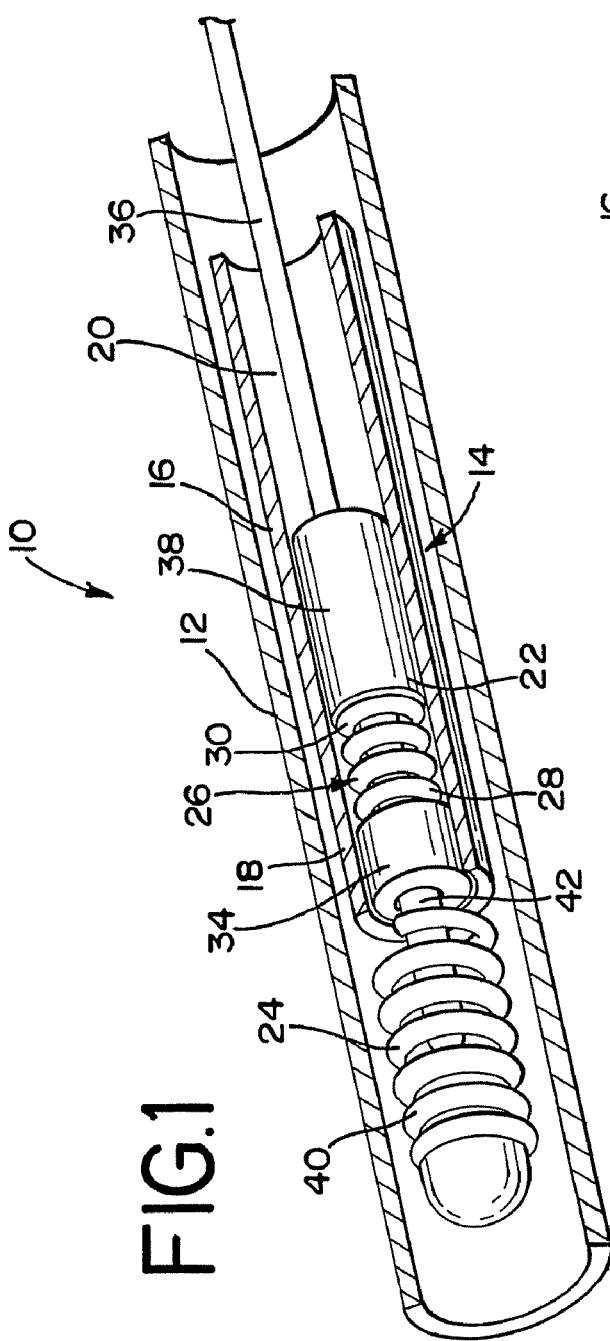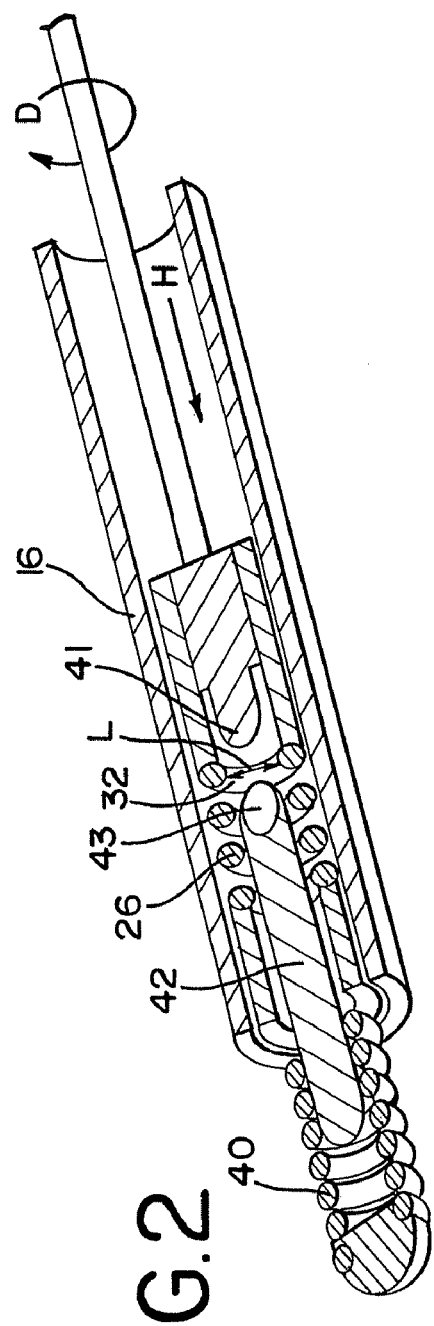

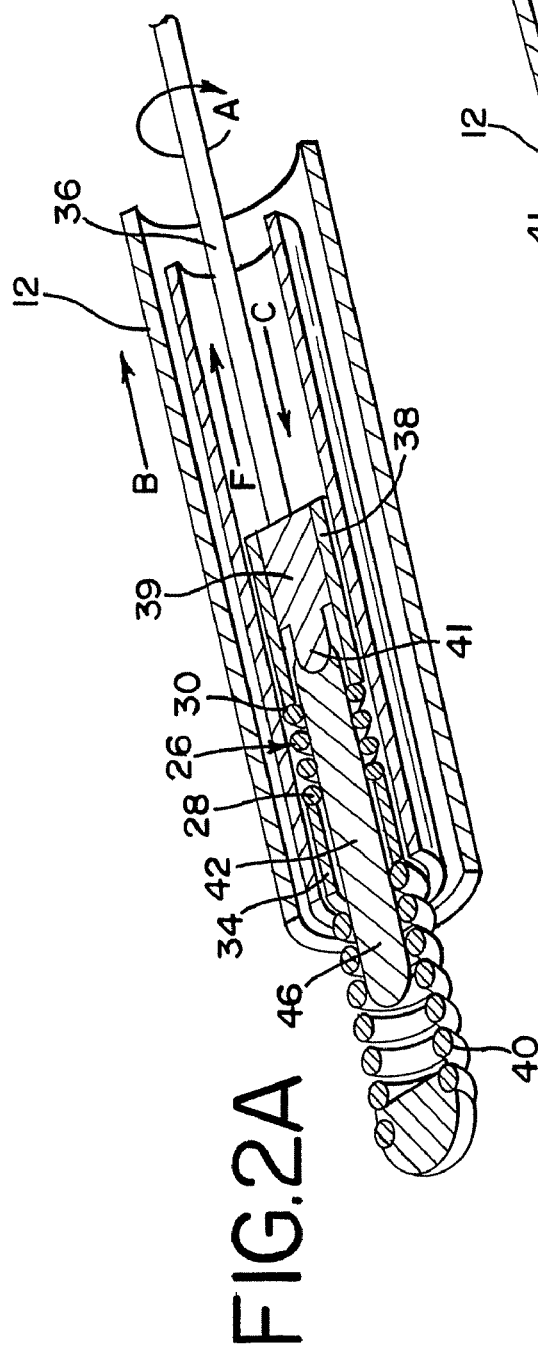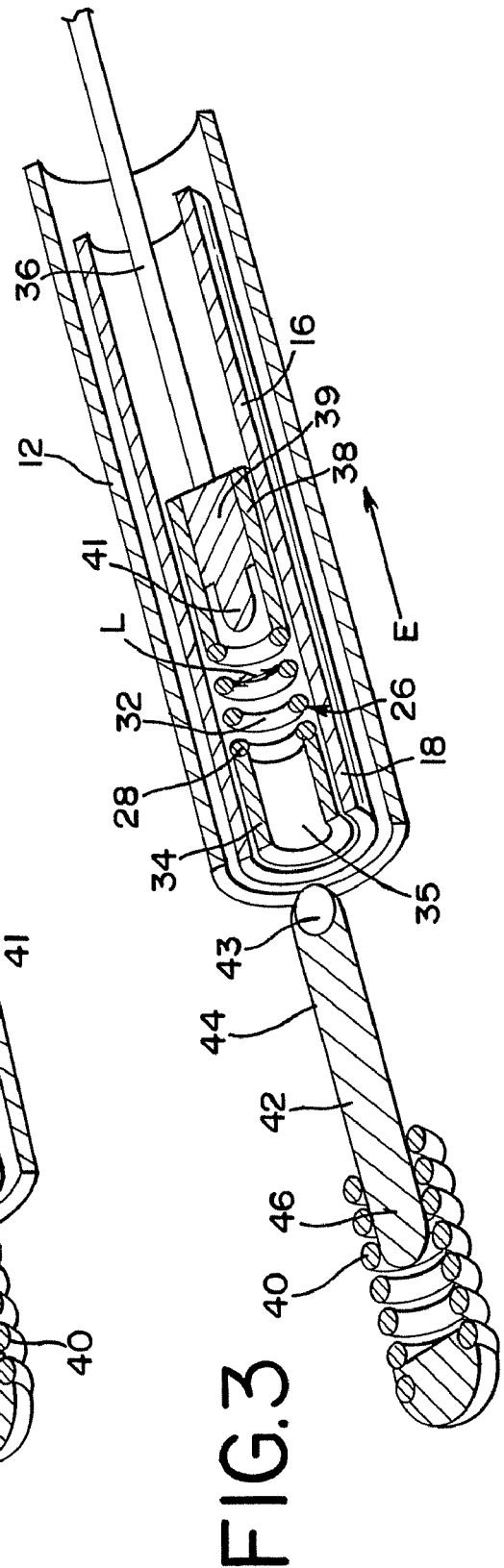

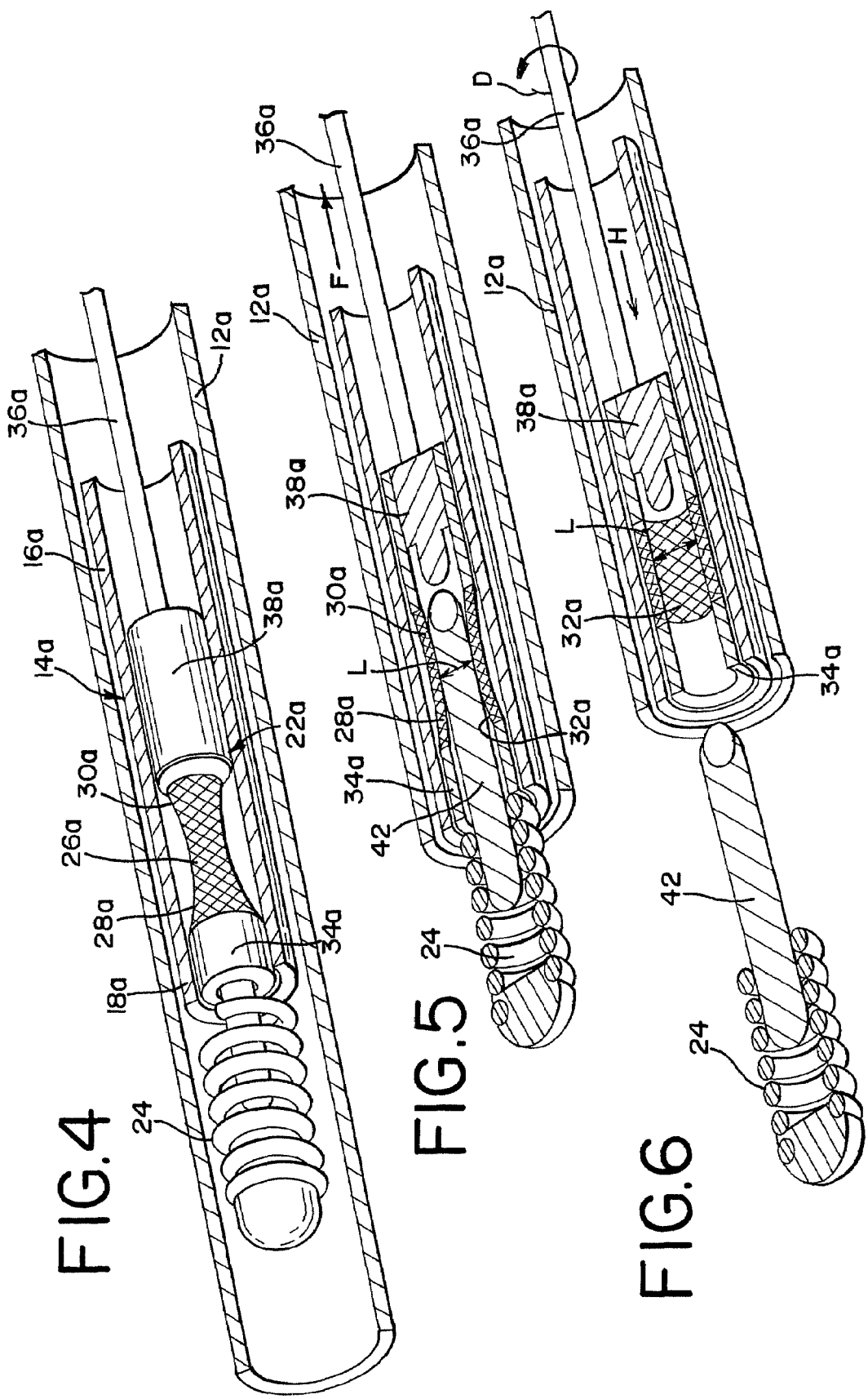

EMBOLIC DEVICE DELIVERY SYSTEM

FIELD OF THE INVENTION

The present invention is related to the delivery of embolic occlusion devices. Disclosed are occlusion device deployment systems and methods for mechanically deploying occlusion devices at a preselected location within a patient, in an accurate and rapid manner. The deployment systems and methods are particularly well suited for deploying an embolic coil at a location of concern within the vasculature, especially intracranially, of a patient.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat defects of intracranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the occlusion device through the catheter and out of the distal end of the catheter into the delivery site. Some of the problems that have been associated with these procedures relate to the accuracy of occlusion device placement. For example, the force employed to eject the occlusion device from the delivery catheter may cause the occlusion device to over shoot the predetermined site or dislodge previously deployed occlusion devices. Also, once the occlusion device is pushed out of the distal end of the catheter, the occlusion device cannot be retracted and may migrate to an undesired location. Often, retrieving and repositioning the occlusion devices requires a separate procedure and has the potential to expose the patient to additional risk.

In response to the above mentioned concerns, numerous devices and release mechanisms have been developed in an attempt to create delivery systems which provide both control of an occlusion device after the device has exited the delivery catheter and a rapid release or detachment mechanism to release the device once the occlusion device is in place. One such device is disclosed in Geremia et al. U.S. Pat. No. 5,108,407, which shows a fiber optic cable including a connector device mounted at the distal end of the fiber optic cable. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that have the potential to interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

Further, the above-identified delivery systems typically require electronic equipment powered by a power source. If the electronic equipment is defective or the power source fails, the procedure may be prolonged while the equipment is repaired or replaced. Prolonging the procedure may expose the patient to additional risk.

Therefore, a need remains for a rapid release vascular occlusion deployment system and/or method that can function without electrical equipment or a power supply, does, not develop chemical debris, is simple to manufacture, flexible and easy to guide through the vasculature of the body, provides excellent control over the occlusion device, and reduces the possibility of interference with other surgical and/or monitoring equipment.

SUMMARY OF INVENTION

The present invention embodies deployment systems and methods for accurately and rapidly deploying an occlusion device at a location of concern within a patient. The deployment system can employ an elongated flexible delivery catheter for guiding a deployment unit to a location of concern within a patient. The deployment unit includes a pusher for pushing and guiding the vascular occlusion device, such as an embolic coil, through the delivery catheter to the location of concern.

In one embodiment, the pusher has a proximal end portion, a distal end portion and a lumen extending along the pusher between the proximal and distal end portions. The pusher also includes a coupling member located in the lumen at the distal end portion of the pusher. The coupling member comprises a constrictor that defines a channel which is sized to receive the headpiece of an embolic device. The constrictor also includes a proximal end portion and a distal end portion. The proximal end portion moves relative to the distal end portion to constrict the constrictor by reducing the internal cross-section of the constrictor. The distal end portion of the constrictor can be connected to the distal end portion of the pusher while the proximal end portion of the constrictor is movable relative to the pusher. In one embodiment, the proximal end portion is able to rotate relative to the distal end portion. In another embodiment, longitudinal or axial movement actuates the constriction operation; for example, proximal end portion movement in the proximal direction and away from the distal end portion activates constriction while opposite movement deactivates constriction.

The proximal end portion of the constrictor can be connected to an elongated member that extends through the lumen of the pusher. The elongated member can be employed to manipulate the proximal end portion of the constrictor relative to the distal end portion.

In one preferred embodiment, the constrictor has a general coil configuration having a plurality of generally adjacent coils. When rotational force or torque is applied to the elongated member, the torque is transferred along the elongated member to the proximal end portion of the constrictor and causes this proximal end portion to rotate. Because the distal end portion of the constrictor is attached to the pusher, rotation of the proximal end portion of the constrictor causes the individual coils to tighten and the cross-sectional extent of the channel defined by the constrictor to reduce in size. When the cross-sectional extent of the channel reduces in size, the constrictor engages or grasps the headpiece of the embolic device. The proximal end portion of the constrictor is then temporarily fixed relative to its distal end portion until it is desired to deploy the embolic device.

In the preferred rotation embodiment, the constrictor has a general coil configuration, and when it is desired to deploy the embolic device, the proximal end portion of the coil constrictor is unfixed and allowed to rotate in the opposite direction, loosing the individual coils and increasing the cross-sectional extent of the channel defined by the coil constrictor. The expanded coil constrictor releases its grasp of the headpiece, deploying the embolic device.

According to one preferred method of the present invention, an embolic device headpiece is inserted into the constrictor channel. The proximal end portion of the constrictor is manipulated, by rotational or longitudinal movements, to reduce the size of the channel so that the constrictor engages or grasps the headpiece. The embolic device is retained by the coupling member, and the pusher is inserted into a delivery catheter. The pusher is employed to guide the embolic device through the delivery catheter to a deployment site within a patient. Once the embolic device is positioned at the deployment site, the proximal end portion of the constrictor is allowed to move back to its non-constriction position to increase the channel's internal size and disengage the constrictor from the embolic device. The pusher can then be retracted in a retrograde manner to release the embolic device at the deployment site.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein:

FIG. 1 is an enlarged partially sectioned view of an occlusion device deployment system in accordance with a preferred embodiment of the present invention;

FIG. 2 is an enlarged partially sectioned view of the occlusion device deployment system shown in FIG. 1 prior to engaging the coupling member and the embolic device headpiece;

FIG. 2A is an enlarged partially sectioned view of the occlusion device deployment system of FIG. 1 shown with the coupling member engaged with the embolic device headpiece;

FIG. 3 is an enlarged partially sectioned view of the occlusion device deployment system of FIG. 1 shown after the occlusion device has been released;

FIG. 4 is an enlarged partially sectioned view of another occlusion device deployment system in accordance with a preferred embodiment of the present invention;

FIG. 5 is an enlarged partially sectioned view of the occlusion device deployment system of FIG. 4 shown with the coupling member engaged with the embolic device headpiece; and FIG. 6 is an enlarged partially sectioned view of the occlusion device deployment system of FIG. 4 shown with an unengaged occlusion device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the occlusion device deployment system of the present invention. The deployment system, generally designated at 10, includes an elongated flexible delivery catheter 12 which can be inserted into the vasculature of a patient and used to guide a deployment unit, generally designated at 14, to a preselected site in a manner generally known in the art. One of ordinary skill in the art will appreciate that the delivery catheter 12 and the deployment unit 14 are much longer than illustrated in the figures.

The deployment unit 14 includes an elongated flexible pusher 16 which has a proximal end portion (not shown) and a distal end portion 18. A lumen 20 extends along the pusher 16 from the proximal end portion to the distal end portion 18. A coupling member 22 is located in the lumen 20 at or near the distal end portion 18 of the pusher 16. The coupling member 22 releasably attaches an embolic device 24 to the distal end portion 18 of pusher 16.

Referring to FIGS. 1-3, the coupling member 22 includes a constriction component 26, which can comprise a spiral or coil member. The constriction component 26 has a distal end portion 28 and a proximal end portion 30. The constriction component 26 has the ability to be moved, such as by rotation or longitudinal movement, from an open configuration to a constricting configuration and to be returned to the open configuration, typically by virtue of or assisted by its resiliency. Typical constricting component materials are metals such as a Nitinol, steel or other material that can withstand stresses without snapping. The material can have resilient characteristics when moved to a configuration other than as pre-shaped.

As illustrated in FIG. 3, the constriction component 26 defines an inner channel 32. The inner channel 32 has a cross-sectional extent "L" that may be reduced and enlarged, depending upon the movement of one or either of the distal or proximal end portions 28, 30 relative to the other. Illustratively, the inner channel 32 defined by the constriction component 26 has a circular cross-section. When the distal or proximal end portion 28, 30 of the constriction component 26 is moved relative to the other end portion, the diameter of the circular channel increases or decreases depending on the direction of movement of the end portions. It will be understood that the cross-sectional shape of the channel 32 defined by constriction component 26 depends on the shape of the constriction component, and thus the cross-sectional shape of the channel can be other than circular; for example, the cross-sectional shape of the channel could be triangular or rectangular.

The proximal end portion 30 of the constriction component 26 is moveable relative to the distal end portion 28 of the constriction component 26. Accomplishing this can include connecting the distal end portion 28 of the constriction component 26 with the distal end portion 18 of the pusher 16 while allowing the proximal end portion 30 of the constriction component 26 to move, rotationally and/or longitudinally, relative to the pusher 16. As illustrated in FIGS. 1 and 2A, the distal end portion 28 of the constriction component 26 may be connected to the distal end portion 18 of the pusher 16 through a tubular member 34 which is connected to both the distal end portion 28 of the constriction component 26 and the distal end portion 18 of the pusher member 16. The tubular member 34 is preferably connected to the distal end portion 18 of the pusher 16 by weld, adhesive or mechanical connection. In another embodiment, the distal end portion 28 of the constriction component 26 may be directly connected to the distal end portion 18 of the pusher 16 without employing tubular member 34, such as by-direct welding, soldering, heat joining, adhesive bonding or mechanical connection. In the embodiments that employ a tubular member to attach these distal end portions together, the tubular member includes a passageway 35 that communicates with the channel 32 defined by the constriction component 26, as illustrated in FIG. 3.

The proximal end portion 30 of the constriction component 26 may be manipulated relative to the distal end portion 28 to constrict and expand or reduce and enlarge the internal cross-sectional extent L of channel 32 defined by the constriction component. When the constriction component 26 comprises a coiled configuration, as illustrated in FIGS. 1-3, the proximal end portion 30 may be rotated relative to the distal end portion 28 in the direction of the wind of the coiled constriction component so that the individual coils tighten to reduce the internal cross-sectioned extent L. When the proximal end portion 30 is rotated in the direction opposite the wind, the individual coils will loosen and the internal cross-section L will enlarge.

Alternatively, the proximal end portion 30 may be manipulated by moving the proximal end portion longitudinally, either proximally or distally in relation to the distal end portion. When the proximal end portion 30 is moved proximally, the individual coils of the coiled constriction component 26 constrict to reduce the internal cross-section L. Conversely, when the proximal end portion 30 is moved distally, the individual coils loosen and the internal cross-section L expands. Additionally, the proximal end portion 30 may be manipulated by a combination of rotational and longitudinal movement.

The proximal end portion 30 of the constriction component 26 may be connected to an elongated member 36 which can be employed to manipulate the proximal end portion 30. In the illustrated embodiment, the coupling member 22 includes a cylindrical section 38 which is connected to the proximal end portion 30 of the constriction component 26. The cylindrical section 38 is in turn connected to the elongated member 36, effectively connecting the proximal end portion 30 of the constriction component 26 to the elongated member 36. Alternatively, the cylindrical member 38 may be eliminated and this proximal end portion 30 may be directly connected to the elongated member 36.

In the embodiments in which the coupling member 22 includes a tubular member 34 and/or a cylindrical member 38 attached to the constriction component's proximal and distal end portions 28, 30, the constriction component 26, tubular member 34 and cylindrical member 38 may be of unitary construction wherein the coupling member 22 is made from a mold or the coupling member 22 is made by cutting a spiral pattern in a tubular structure to form a constriction component having a coil configuration. Alternatively, constriction component 26, the tubular member 34 and the cylindrical member 38 can each be separate segments which are connected together, for example, by weld or adhesive.

Referring to FIG. 3, the cylindrical member 38 may include a center insert 39 that includes a projection such as ball 41 which mates with an indent such as socket 43 located at the proximal end portion 44 of the headpiece 42. Alternatively, a projection can be in the headpiece and an indent in the insert. Other shapes are possible. This mating function aids in supporting the embolic device 24 and centering the headpiece 42 within the coupling 22.

The pusher element 16 can be any suitable type of delivery tube generally known in the art that has sufficient column strength to push an embolic device through a delivery catheter and has sufficient flexibility to be guided through tortuous pathways within the vasculature of a patient. For example, the pusher can be comprised of a coil wound wire or a flexible polymer sheath. Additionally, the pusher 16 should have the ability to resist torque applied to the pusher during connection of the embolic device to the coupling member, as described below.

The elongated member 36 is preferably a wire that is comprised of a metallic or polymeric material which has tensile and flex properties that allow the elongated member 36 to be easily guided through tortuous paths within the patient. The elongated member 36 should also have sufficient structural integrity to transmit torque along the elongated member 36 without shearing or buckling, and to withstand pushing and/or pulling without snapping or breaking.

The embolic device 24 is preferably an embolic device assembly that includes an embolic element 40 and a headpiece 42. As illustrated in FIGS. 1-3, the embolic device headpiece 42 can be a shaft-like structure which has a proximal end portion 44 and a distal end portion 46. The distal end portion 46 of the headpiece 42 is connected to the embolic element 40 and the proximal end portion 44 is sized to fit within the channel 32 of the constriction component 26. Illustratively, the embolic device 24 comprises the headpiece 42 and the embolic element 40 as separate components that are secured together; however, it will be understood by one of ordinary skill in the art that the embolic element and the headpiece can be of a unitary construction.

The embolic element 40 is preferably an embolic coil which can be of the type which takes a substantially linear configuration for being advanced through the delivery catheter 12 and a randomly oriented relaxed condition after it is released from the catheter. Alternatively, the embolic element 40 may be any other type of embolic element which may take on various forms and configurations, such as hydrogels, foams, bioactive coils, braids, cables and hybrid devices.

To attach the embolic device 24 to the delivery unit 14, referring to FIGS. 2 and 2A, the proximal end portion 44 of the embolic device headpiece 42 is inserted into the channel 32 of the constriction component 26 until the indent, such as the illustrated socket 43 at the proximal end portion 44 of the headpiece 42, engages the projection, such as the illustrated ball 41 of the coupling member 22. As illustrated in FIG. 2, the cross-sectional extent L of the channel 32 defined by the constriction component 26 is preferably larger than the outer diameter of the embolic device headpiece 42. Referring to FIG. 2A, the elongated member 36 is employed to manipulate the proximal end portion 30 of the constriction component 26 to constrict the constriction component. In one preferred method, torque is applied to the elongated member 36 in the direction of the wind of the coil, as indicated by arrow A. The torque may be applied by rotating a distal end portion of the elongated member by hand or some other mechanical means.

Applying torque to the elongated member 36 causes the proximal end portion 30 of the constriction component 26 to rotate relative to the pusher 16 while its distal end portion 28, which is attached to the pusher, stays stationary relative to the pusher. Thus, rotating the proximal end portion 30 of the constriction component 26 in the direction of the illustrated coil wind causes reduction of the cross-sectional extent L, or constriction, of the channel 32 defined by the constriction component 26.

In an alternative method, the elongated member 36 may be retracted or pulled proximally as indicated by arrow F. This will cause the proximal end portion 30 of the constriction component 26 to move proximally relative to the distal end portion 28. When the proximally end portion 30 moves proximally, the individual coils of the constriction component 26 constrict and the internal cross-section L of channel 32 reduces.

Reducing the cross-sectional extent L of the channel 32 causes the constriction component 26 to engage or grasp the headpiece 42, securing the embolic device 24 to the distal end portion 18 of the pusher 16. The elongated member 36, whether rotated or moved longitudinally, is then temporarily fixed relative to the pusher 16, which can include the use of a fixation device (not shown) to retain the coupling-headpiece engagement.

FIGS. 4-6 illustrate an alternative embodiment in accordance with the present invention. In this embodiment, the coupling member 22a of deployment unit 14a includes a braided constriction component 26a that comprises a tubular shaped braided element. The braided element may be made from woven wire or polymer strands. Similar to the embodiment illustrated in FIGS. 1-3, the distal end portion 28a of the constriction component 26a can be connected to the distal end portion 18a of pusher 16a via a tubular element 34a, and the proximal end portion 30a can be movable relative to the pusher. Thus, the proximal end portion 30a is movable, longitudinally and rotationally, relative to the distal end portion 28a.

The proximal end portion 30a of the constriction component 26a can be connected to a cylindrical member 38a which is in turn connected to an elongated member 36a. The elongated member 36a can be employed to manipulate the proximal end portion 30a to cause the braided constriction component 26a to constrict and expand. For example, referring to FIG. 5, the elongated member 36a can be retracted proximally, as indicated by arrow F, to move the proximal end portion 30a of the constriction component 26a away from its distal end portion 28a. Moving the proximal end portion 30a away from the distal end portion 28a causes the braided constriction component 26a to lengthen axially and the internal cross-section L of the channel 32a defined by the constriction component 26a to reduce. The action of the braided constriction component is very similar to the braided finger trap gag toy.

The elongated member 36a may then be fixed relative to the pusher 16a to keep the braided constriction component 26a in the constricted configuration. When the elongated member 36a is unfixed relative to the pusher 16a, the proximal end portion 30a is able to move towards the distal end portion 28a, preferably assisted by the resiliency of the braided constriction component, so that the constriction component 26a returns to the expanded configuration. Alternatively, the elongated member 36a can be used to move the proximal end portion 30a towards the distal end portion 28a.

To attach an embolic device 24 to the delivery unit 14a, headpiece 42 of the embolic device is inserted into channel 32a of the braided constriction component 26a. Preferably, the cross-sectional extent L of the channel 32a is larger than the embolic device headpiece 42. Referring to FIG. 5, the elongated member 36a is retracted proximally, as indicated by arrow F, to move the proximal end portion 30a away from the distal end portion 28a.

Moving the proximal end portion 30a away from the distal end portion 28a causes the internal cross-section L of the channel 32 to reduce. Thus, the braided constriction component 26a constricts to engage or grasp the headpiece 42, securing the embolic device 24 to the distal end portion 18a of the pusher 16a. The elongated member 36a is then temporarily fixed relative to the pusher 16a to retain the coupling-headpiece engagement.

It is also contemplated that the elongated member 36a could be employed to rotate the proximal end portion 30a relative to the distal end portion 28a. Rotation of the proximal end portion 36a causes the braided constriction component 26a to wrap around or snare the headpiece 42 to secure it to the pusher.

Deployment of the embolic device 24 will generally be described in relation to FIGS. 1-3. After the embolic device 24 has been attached to the pusher 16, the delivery catheter 12 can be inserted into the vasculature system of a patient, and the distal end portion of the catheter can be positioned at a preselected location within a blood vessel, typically in conjunction with other devices and professional procedures as generally known in the art. The delivery unit 14 is inserted into a proximal end portion of the catheter 12, and the delivery unit 14 is advanced through the delivery catheter 12 until the embolic device 24 reaches the distal end portion of the delivery catheter 12.

Referring to FIG. 2A, once the embolic device 24 reaches the distal end portion of the delivery catheter 12, the embolic device 24 may be moved out of the distal end portion of the delivery catheter 12 by moving the delivery catheter in a retrograde manner as indicated by arrow B, by advancing the pusher 16 as indicated by arrow C, or by a combination of moving the delivery catheter in a retrograde manner and advancing the pusher.

The embolic device 24 preferably includes at least one radiopaque marker so that the position of the embolic device can be monitored by fluoroscopy. After the embolic device 24 has exited the delivery catheter 12, if it is determined that the embolic device 24 is in the wrong position and/or a different embolic device is required, the pusher 16 can be retracted to move the embolic device 30 back into the delivery catheter 12. Once in the delivery catheter 12, the embolic device can be repositioned or completely removed from the patient.

After it has been determined that the embolic device 24 is at the desired location within the patient, the fixation device (not shown), which has temporality fixed the elongated member relative to the pusher, is removed or loosened to allow the constriction component 26 to return to its expanded configuration. For example, if the constriction component has been constricted by rotation of the proximal end portion, torque is released as indicated by arrows D of FIG. 2 and FIG. 6. Alternatively, if the constriction component has been constricted by moving the proximal end portion longitudinally away from the distal end portion, the elongated member and the proximal end portion move distally as indicated by arrows H in FIG. 2 and FIG. 6.

Upon release of elongated member 36, the cross-sectional extent L of the channel 32 of the constriction component 26 expands, preferably due to the resiliency of the constriction component, and the constriction component 26 disengages or releases its grasp of the coil headpiece.42. Referring to FIG. 3, the pusher 16 and the delivery catheter 12 may then be retracted as indicated by arrow E to deposit the embolic device 24.

After the release, the pusher 16 can now be retracted through the delivery catheter 12 and removed from the patient. If desired, additional embolic devices may be deployed in a similar manner to that described above.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An embolic device delivery system, comprising:
a pusher having a proximal end portion and a distal end portion and a lumen;
a constriction component disposed at or near the distal end portion of the pusher within the lumen of the pusher, said constriction component defining an inner channel having a first cross-sectional extent that is sized to allow at least a portion of an embolic device to be received within the channel;
said constriction component having a proximal end portion and a distal end portion with said inner channel therebetween, said proximal end portion of the constriction component being movable relative to its said distal end portion;
said distal end portion of the constriction component is held stationary relative to the pusher, the proximal end portion of the constriction component is movable relative to the distal end portion and to the pusher, and the distal end portion of the constriction component is connected to the distal end portion of the pusher; and
whereby upon movement of the proximal end portion of the constriction component relative to its said distal end portion, the inner channel defined by the constriction component changes from the first cross-sectional extent to a second smaller cross-sectional extent wherein the constriction component secures the at least a portion of the embolic device within the inner channel.

2. The delivery system of claim 1 wherein the constriction component includes a coil, and the channel defined by the coil has a circular configuration.

3. The delivery system of claim 1 wherein the constriction component comprises a braided tubular shaped element.

4. The delivery system of claim 1 wherein the proximal end portion of the constriction component is rotatable relative its distal end portion.

5. The delivery system of claim 1 wherein the proximal end portion of the constriction component is movable longitudinally relative to its distal end portion.

6. The delivery system of claim 1 further including an elongated member connected to the proximal end portion of the constriction component for manipulation of the proximal end portion of the constriction component.

7. The delivery system of claim 6 wherein the elongated member comprises a wire.

8. The delivery system of claim 1 wherein the first cross-sectional extent of the channel defined by the constriction component is larger than the at least a portion of the embolic device.

9. An embolic device delivery system, comprising:
a pusher having a proximal end portion, a distal end portion and a lumen extending along the pusher;
a tubular coupling located within the lumen at or near the distal end portion of the pusher, said tubular coupling defining a channel which is sized to receive at least a portion of an enibolic device, said tubular coupling having a proximal end section, a middle section, and a distal end section, and the distal end section of the coupling is connected to the pusher and held stationary relative to the pusher, the proximal end section of the coupling being movable relative to the distal end section of the coupling; and
the middle section of the tubular coupling having an inner cross-sectional extent which changes from a first dimension to a second dimension upon movement of the proximal end section of the coupling relative to the distal end section of the coupling.

10. The delivery system of claim 9 wherein the middle section comprises a coiled configuration.

11. The delivery system of claim 9 wherein the middle section comprises a braided element.

12. The delivery system of claim 1 wherein the proximal end portion of the constriction component is rotatable relative its distal end portion.

13. The delivery system of claim 1 wherein the proximal end portion of the constriction component is movable longitudinally relative to its distal end portion.

14. The delivery system of claim 9 further including a narrow elongated member connected to the proximal end section of the coupling.

15. A combination embolic device and an embolic device delivery system, comprising:
an embolic device having a proximal end portion and a distal end portion;
an embolic device headpiece located at the proximal end portion of the embolic device;
a pusher having a proximal end portion, a distal end portion and a lumen extending along the pusher;

a constrictor located in the lumen at or near the distal end portion of the pusher, said constrictor defining an inner channel having a first cross-sectional extent, said embolic device headpiece located within the channel;

said constrictor having a proximal end portion and a distal end portion with said inner channel therebetween, said proximal end portion of the constrictor being movable relative to its said distal end portion;

said distal end portion of the constrictor component is held stationary relative to the pusher, and the proximal end portion of the constriction component is movable relative to the pusher; and whereby upon movement of the proximal end portion of the constrictor relative to its said distal end portion, the inner channel defined by the constrictor changes from the first cross-sectional extent to a second smaller cross-sectional extent wherein the constrictor grasps the embolic device headpiece.

16. The combination of claim 15 wherein the constrictor comprises a coil, and the channel defined by the coil has a circular configuration.

17. The combination of claim 15 wherein the constrictor comprises a braided element.

18. The combination of claim 15 further including an elongated member connected to the proximal end portion of the constrictor to manipulate the proximal end portion of the constrictor.

19. A method of employing a pusher to deliver an embolic device to a location within the vasculature of a patient, the pusher including a constrictor located at a distal end portion of the pusher, said constrictor defining a channel having a cross-sectional extent, said constrictor having a proximal end portion, a distal end portion, and a constriction portion between the proximal and distal end portions, said distal end portion of the constrictor being connected to the distal end portion of the pusher, and said proximal end portion of the constrictor movable relative to the distal end portion of the constrictor, comprising:

inserting a portion of an embolic device into the channel defined by the constrictor;

moving the proximal end portion of the constrictor to decease the cross-sectional extent of the channel so that the constrictor grasps the portion of the embolic device located in the channel;

fixing the proximal end portion of constrictor relative to the distal end portion of the constrictor;

manipulating the pusher to guide the embolic device to a preselected location within the vasculature of a patient;

increasing the cross-sectional extent of the constriction portion of the channel by releasing the proximal end portion of the constrictor relative to its distal end portion which remains connected to the distal end portion of the pusher, thereby releasing the portion of the embolic device from the constrictor and thus from the pusher.

20. The method of claim 19 wherein moving the proximal end portion of the constrictor comprises rotational movement.

21. The method of claim 19 wherein moving the proximal end portion of the constrictor comprises longitudinal movement.

22. The method of claim 19 wherein moving the proximal end portion of the constrictor comprises a combination of rotational movement and longitudinal movement.

* * * * *